United States Patent [19]

Eadie

[11] Patent Number: 5,744,102
[45] Date of Patent: Apr. 28, 1998

[54] SOLID PHASE SYNTHESIZER

[75] Inventor: James Scott Eadie, San Diego, Calif.

[73] Assignee: Chugai Biopharmaceuticals, Inc., San Diego, Calif.

[21] Appl. No.: 593,631

[22] Filed: Jan. 30, 1996

[51] Int. Cl.⁶ ........................................................ C08F 2/00
[52] U.S. Cl. ........................... 422/131; 422/134; 530/333; 530/334
[58] Field of Search ..................................... 422/131, 134; 530/333, 334

[56] References Cited

U.S. PATENT DOCUMENTS

| | | | |
|---|---|---|---|
| 3,276,751 | 10/1966 | Svensson et al. | 259/3 |
| 3,764,112 | 10/1973 | Jelley et al. | 259/57 |
| 4,748,002 | 5/1988 | Neimark et al. | 422/116 |
| 5,091,503 | 2/1992 | Inatome et al. | 528/272 |
| 5,186,824 | 2/1993 | Anderson et al. | 210/198.2 |
| 5,324,483 | 6/1994 | Cody et al. | 422/131 |
| 5,429,807 | 7/1995 | Matson et al. | 422/131 |
| 5,552,322 | 9/1996 | Nemoto et al. | 435/287.2 |

FOREIGN PATENT DOCUMENTS

| | | |
|---|---|---|
| 0386238 | 7/1988 | European Pat. Off. |
| 0503683 | 9/1992 | European Pat. Off. |
| 8501224 | 3/1985 | WIPO |
| 9000190 | 1/1990 | WIPO |

OTHER PUBLICATIONS

Seliger, "Ch. 17—Scale–Up of Oligonucleotide Synthesis," *Methods in Molecular Biology 20, Protocols for Oligonucleotides and Analogs*, S. Agrawal ed., Humana Press, Totowata, New Jersey, pp. 391–392 (1993).

Sinha, "Ch. 18—Large Scale Oligonucleotide Synthesis Using the Solid Phase Approach," *Methods in Molecular Biology 20, Protocols for Oligonucleotides and Analogs*, S. Agrawal ed., Humana Press, Totowata, New Jersey, pp. 440–442 (1993).

*Primary Examiner*—Nina Bhat
*Attorney, Agent, or Firm*—Lyon & Lyon LLP

[57] ABSTRACT

Solid phase synthesizer and method of use for synthesis of a polymer. The synthesizer has a generally horizontal elongated vessel for holding a solid support and liquid having two ends, each end having a porous blocker to prevent the solid support from leaving the vessel but allowing passage of the liquid from the vessel. A particulate solid support is held within the vessel and has a size sufficient to prevent passage through the blocker.

40 Claims, 2 Drawing Sheets

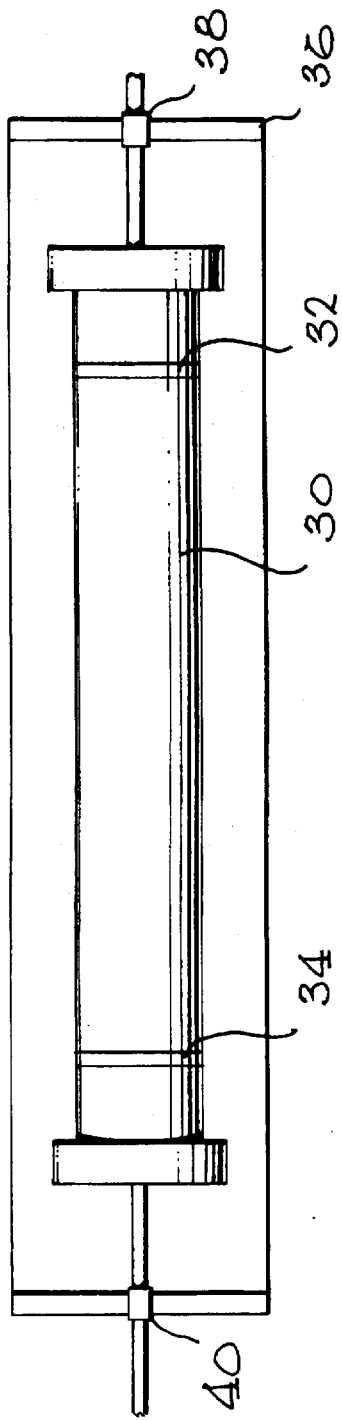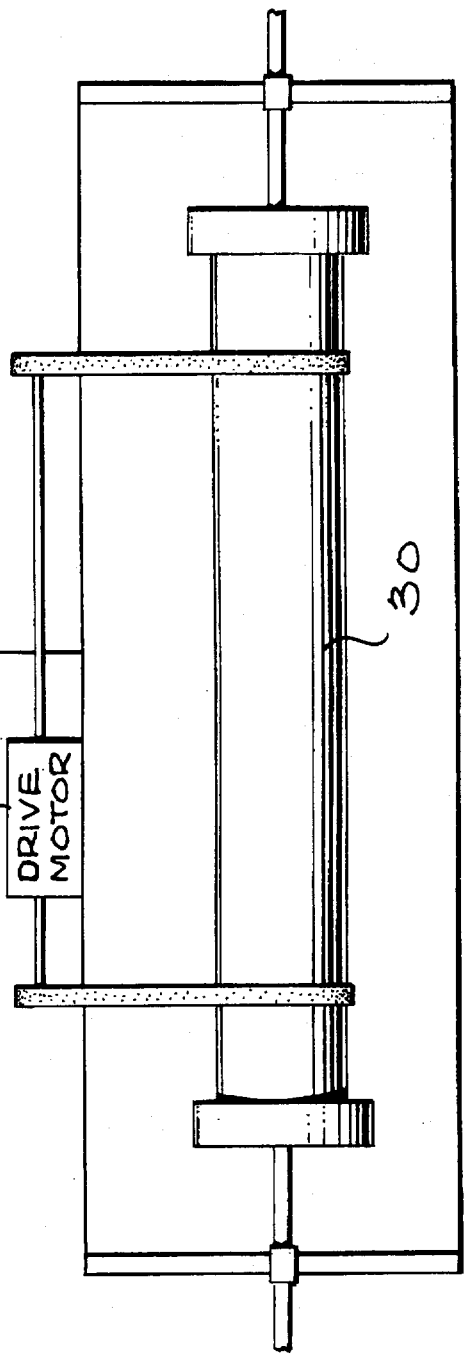

5,744,102

SOLID PHASE SYNTHESIZER

BACKGROUND OF THE INVENTION

This invention relates to methods and apparatus for synthesis of polymers, such as DNA, RNA, and proteins.

Current large scale commercial DNA synthesis is limited to approximately 2 mmole, although reports of larger syntheses are made. The 2 mmole scale may be sufficient for producing oligonucleotide drug compounds for research, preclinical development (toxicology/pharmacology), and for phase I clinical trials but might be insufficient for phase II/III clinical trial requirements or for actual manufacturing for post-clinical trial sales. This is shown graphically in FIG. 3, where the manufacturing requirements for a drug are shown in relation to dose, patient number and grams of drug required daily.

Current DNA synthesis technology uses vertical generally cylindrical-shaped, columns or reaction vessels. These chambers hold the solid support (typically CPG (controlled pore glass)) on which the synthesis occurs. The solid support is confined to the reaction chamber by the use of one or more frits (porous glass filters). Fluid flow is typically vertical and may flow up from the bottom of the vessel or vice versa. Commercially-available pre-packed columns typically come in the 1–10 µmol size (or less). The current largest commercially available reaction vessel is 2 mmol (the Milligen 8800 DNA synthesizer). The approximate internal volume is 300 ml, with about 22 ml occupied by the solid support. For the Milligen design, reagents are dispensed through the top and waste leaves through the bottom of the reaction chamber.

Seliger, 20 *Methods in Molecular Biology, Protocols for Oligonucleotides and Analogs*, p. 391, 1993, Chapter 17, "Scale-Up of Oligonucleotide Synthesis", indicates that "several grams of potential antisense chemotherapeutics are required for pharmacokinetic studies, and preclinical and clinical testing will necessitate quantities up to the kilogram range, which constitutes a 1000-fold, later an even $10_6$–$10_7$, increase of the scale of present day preparations." Id. at 392. Many examples are provided of how the chemistry can be altered to enhance the synthesis of the polymers. The article ends by quoting T. Geiser as follows: "this necessitates 'the development of new technology, that permits the cost-effective production, characterization and quality assurance of up to kilogram quantities of oligonucleotide material'. Solution methods may play a role in these new developments."

Sinha, 20 *Methods in Molecular Biology, Protocols for Oligonucleotides and Analogs*, Chapter 18, "Large-Scale Oligonucleotide Synthesis Using the Solid-Phase Approach", describes at page 440 a general instrument design and in particular, the model 8800 DNA synthesizer. At page 442 it states that "it is very essential to have proper fluidization of the large amount of supports. Fluidization in this approach is effected by bubbling dry gas (argon) through the bottom of a reactor, resulting in complete suspension of the support." Significant detail is provided of the chemical methodology required for optimum synthesis.

The publications noted above are incorporated in totality herein by reference for their description of oligonucleotide synthesis and associated apparatus and chemical steps.

SUMMARY OF THE INVENTION

Applicant provides an apparatus and method for synthesis of polymers such as DNA, RNA, peptides, carbohydrates or for various combinatorial libraries, by use of a vessel which is held in a generally horizontal manner. Applicant has determined that a limitation of the scalability of polymer synthesis is the use of solid supports in a generally vertical vessel. The use of a vertical vessel can limit the ability of the user to synthesize large amounts of the desired polymer. If a horizontal vessel is used, the scale of synthesis can be increased many fold, making possible synthesis of commercially necessary quantities of therapeutic agents (see FIG. 3).

Thus, in a first aspect, the invention features a solid phase synthesizer, for synthesis of a polymer, having a generally horizontal elongated vessel for holding a solid support and liquid. The vessel has two ends, each having a porous blocker (e.g., a frit) to prevent the solid support from leaving the vessel but allowing passage of the liquid from the vessel. The vessel includes a particulate solid support held within the vessel having a size sufficient to prevent passage through the porous blocker. The synthetic reaction will take place on this solid support.

In preferred embodiments, the vessel is generally cylindrical, and has a generally smooth, non-smooth, or serrated inner surface; the cylinder may include an internal screw, blades or a mixer (e.g., mixing bars) adapted to enhance mixing of the solid support and liquid; alternatively or in addition the vessel may include an agitator, vibrator or vortexer adapted to agitate, rock or vortex the solid support and liquid within the vessel.

In more preferred embodiments, the synthesizer includes a rotator adapted to rotate the vessel about its horizontal axis, e.g., the rotator is stepped to allow different rotational speeds of the vessel and the vessel is adapted to rotate at a speed sufficient to cause mixing of the solid support with the liquid, but insufficient to cause significant fragmentation of the solid support; a positioner is also provided and adapted to move the vessel from a horizontal position to a vertical position, and back again; the vessel may have an internal length from 5 to 100 centimeters, most preferably from 15 to 30 centimeters, and it preferably has an internal diameter of 3 to 15 centimeters, e.g., 5 to 10 centimeters, so that it has a size sufficient to allow synthesis of the polymer at a scale of 20, 50, 100 or even 500 millimoles or greater.

In yet other preferred embodiments the synthesizer is adapted to tilt or rock the vessel; a pump (e.g., gas-activated) is provided for provision of chemicals to the vessel, e.g., under pressure; the vessel is maintained under anhydrous conditions; and the synthesizer is adapted to synthesize an oligodeoxyribonucleotide, an oligoribonucleotide (such nucleotides may include modifications well known in this art, e.g., at the 2', 3' or 5' positions of the sugar moiety, or may even include sugar moieties lacking a base or modifications at the phosphate linkage), polypeptide, or a combinatorial library (e.g., the vessel is siliconized or treated to reduce unwanted chemical reactions).

In a related aspect, the invention features an improved method for synthesis of a polymer by providing a solid phase synthesizer for synthesis of the polymer and introducing chemicals into the synthesizer in a desired order. The improvement is the use of a solid phase synthesizer having a generally horizontal elongated vessel for holding a solid support and liquid as described above.

Applicants' invention overcomes problems of reagent delivery and potential channeling of reagents which can be observed in vertical columns. Such problems can reduce yield of polymer, and the quality of the polymer. The ability to rotate the horizontal column or to provide other mixing means within the column or outside of the column prevents incomplete chemical reactions and thus can enhance yields of the synthesis of the polymer. Such columns may include suitable particles or beads, such as those susceptible to compression or breakage (as described herein), e.g., CPG, polymeric beads, silica gels, methyl acrylate, polystyrene, Teflon®, and other suitable organic polymers.

Applicant has performed preliminary experiments (as described below) with a prototype apparatus and determined that the beads generally used in synthesis of DNA, termed CPG, are able to operate efficiently in such an apparatus without noticeable mechanical breakdown of the beads. With such an apparatus, kilogram quantities of DNA can be synthesized using a column of only one meter in length and 15 centimeters in diameter. (See, Table 1.)

TABLE 1

| Reaction Vessel Scale Parameters | | | | |
|---|---|---|---|---|
| Cylinder Length (cm) | Cylinder Diameter (cm) | CPG Volume* (ml) | Scale (mM) | Yield (g) |
| 15 | 5 | 147 | 12 | 18 |
| 30 | 5 | 295 | 23 | 35 |
| 30 | 7 | 577 | 47 | 71 |
| 100 | 5 | 982 | 77 | 116 |
| 100 | 10 | 3927 | 320 | 464 |
| 100 | 14.7 | 8486 | 668 | 1002 |

*based on ½ height packing

Many means of mechanical mixing can be used so long as such means do not significantly affect the integrity of the solid phase support. Unlike vertical columns where the weight of the beads themselves can be detrimental to those beads, Applicant notes that a horizontal vessel allows the depth of the beads to be maintained at a safe level without reducing the volume of solid phase support that can be used.

One of the advantages of increasing the scale of synthesis to such a large degree is that larger lots of chemicals can be produced. Such lots must generally be analyzed, for example, for approval by federal agencies. The production of one large lot rather than several small lots reduces the number of tests that need to be performed on any batch of product.

Applicant's invention can be applied in many existing polymer synthesis machines by simply adapting the generally vertical column used therein to a horizontal column. Any number of different rotating or mixing means can be used with such an apparatus, and those in the art will recognize that many different designs having equivalent function can be used to ensure adequate mixing of the solid phase and liquid reagents. Applicant has determined that it is in some circumstances easier to fill a horizontal column when it is held in a vertical position and then moving that vertical column to the horizontal position. Indeed, such movement from the horizontal to the vertical position can be used throughout the synthesis process to facilitate convenient input of fresh chemicals at each stage. Such a movement step can be readily introduced into existing apparatus. In addition, while rotation of the column is desireds it will be evident that a mechanism for tilting or rocking of the column, simultaneously or separately from the rotating, can be readily introduced into such an apparatus to ensure thorough mixing of the contents of the column. By altering the inner surface of the column so that it is either smooth, serrated or roughened in other ways, those in the art will recognize that further more efficient mixing can be achieved. Thus, all of the features noted above aim toward enhancing mixing of the solid phase and liquid while the vessel is held in a generally horizontal position.

Other features and advantages of the invention will be apparent from the following description of the preferred embodiments thereof, and from the claims.

DESCRIPTION OF THE PREFERRED EMBODIMENT

The figures will first briefly be described.

BRIEF DESCRIPTION OF THE DRAWINGS

FIGS. 2A and 2B are longitudinal sectional views of a horizontal column of a reaction chamber.

HORIZONTAL CHAMBER

Figure 1:
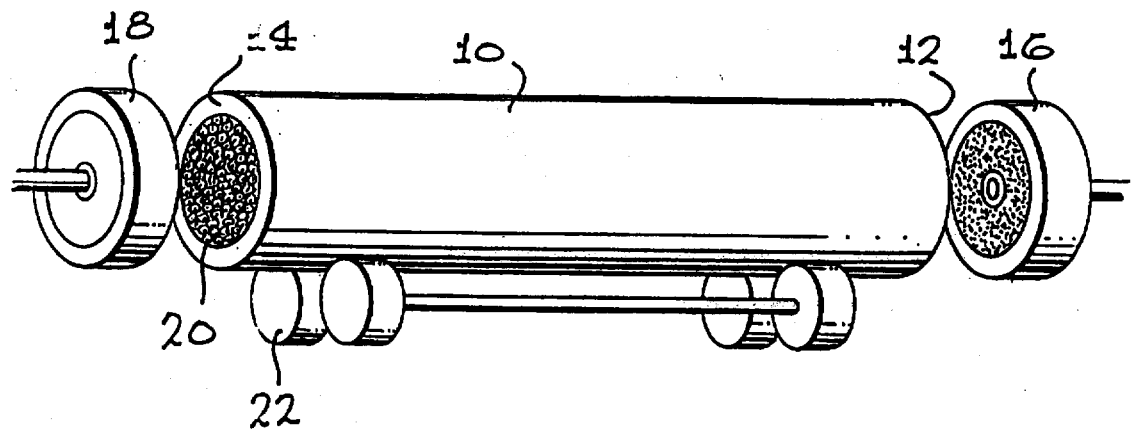
FIG. 1 is a schematic of a DNA synthesis reaction chamber.
Figure 3:
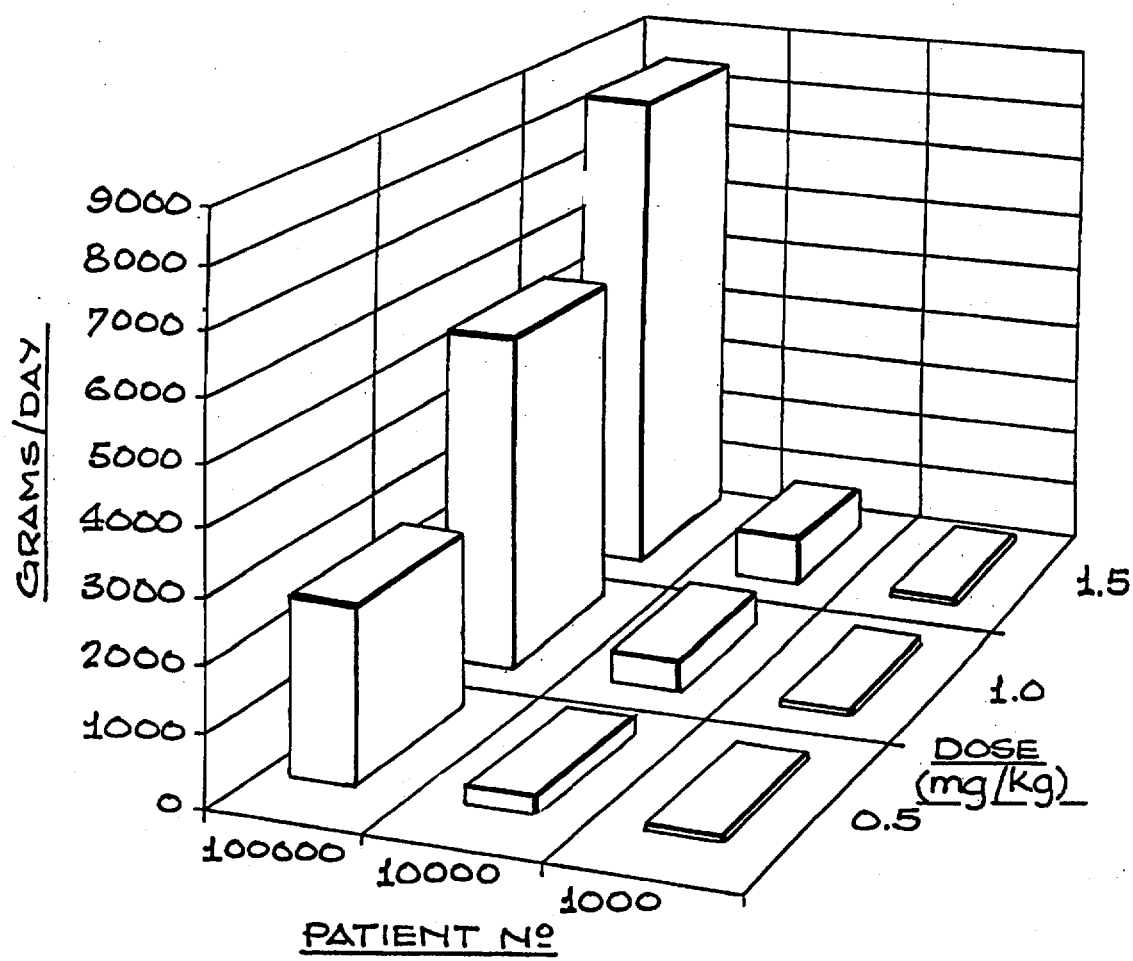
FIG. 3 shows graphically the manufacturing requirements for a successful drug.

This invention concerns a reaction chamber based on a rotating horizontal cylinder instead of a stationary vertical cylinder (see FIGS. 1 and 2A/B). This approach has several advantages:

A larger scale can be readily accommodated without linear increases in bed height. For example, using a 30 cm long cylinder with a 7.0 cm inside diameter filled to half-height (3.5 cm) will give approximately a 50 mmol scale with no increase in bed height (see Table 1) when compared to the Milligen 8800 2 mmol reaction vessel. Bed height is typically a limitation due to the tendency of the CPG particles to pack and possibly crush under their own weight, or to form channels which will bypass areas of the particles available for chemical reactions. Flow dynamics become less optimal with increasing bed height thus influencing chemical efficiencies and ultimately decreasing overall synthetic yields.

The horizontal design allows for gentle agitation of the solid support by controlled rotation. This agitation is an improvement over the existing "fluidized bed" technology and/or passive diffusion of chemicals and solvents into and out of the solid support. Mixing in previously existing machines is typically achieved with fluid flow or by mechanical manipulation such as vibration (Systech instrument) or vortexing (Applied Biosystems instrument) with the vessel retained in the vertical position.

The present design allows for a tilting/rocking movement as necessary to enhance mixing of the solid support. Tilting the apparatus will also facilitate rapid and complete addition/removal of reagents/solvents.

If additional agitation is desired, the rotating horizontal cylinder design allows for the convenient addition of internal mixing bars (of linear or spiral configuration, as examples).

Prototype

In order to establish the use of the horizontal chamber, a working prototype was fashioned from commercially available materials. Glass liquid chromatography columns were used for the reaction chamber. This is a convenient device to test the chamber because of the normal fluid delivery type of application. A cell culture roller bottle apparatus was used to provide mechanical rotation of the chamber. This roller has a variable speed control.

For the sake of establishing proof-of-principle, reagents were added manually to the device. Those in the art will recognize that in actual use such reagents will enter and exit through tubing at each end of the device. Inline swivels or some equivalent device will allow free rotation while maintaining fluid flow. Such a device will facilitate a closed system and will allow direct interface with an existing DNA, RNA or peptide synthesizer, such as the Milligen 8800. A closed system is preferred since DNA synthesis chemistry contains anhydrous steps.

EXAMPLE 1

Mechanical integrity of CPG

In order to ensure that the solid support used within a vessel was able to withstand the mechanical forces to be useds some preliminary tests were run. These mechanical integrity tests were performed on the CPG solid support. For this experiment, CPG was mechanically manipulated under mock synthesis conditions over a period of time representative of that necessary to synthesize a 26 base oligonucleotide (about 24 hr). Samples of the CPG were removed and assayed for particle size distribution. No significant changes were observed over the time course of the experiment.

EXAMPLE 2

Prototype Vessel

Referring to FIG. 1, a vessel 10 is provided for a DNA synthesis reaction chamber. This vessel is a generally cylindrical chromatography column, and is held in a horizontal orientation along its horizontal axis. The size can be chosen in accord with the desired yield. One example of a column can hold about 8 g CPG (for a 800 μmole synthesis). Larger columns can be used to give a greater product yield (see Table 1), e.g., at least about 20 mM synthesis or greater. At each end 12 and 14 is provided a fritted filter 16 and 18, respectively, which prevents passage of a solid phase support 20 (CPG) held within vessel 10 but allows passage of liquid from vessel 10. The CPG may be added with vessel 10 held in a vertical or horizontal position or may be filled by hand prior to use in an automated synthesizer. The vessel is then laid along its horizontal axis. Vessel 10 is held on a rotating apparatus 22 powered by an electric motor which allows gentle rotation of solid phase support 20 and any liquid within column 10.

Referring to FIG. 2A, column 30 is provided with two fritted glass filters 32 and 34 held within an apparatus 36 which allows rotation of column 30 about its horizontal axis. Two in-line swivel connectors 38 and 40 are provided at each end of column 30 to allow free rotation of column 30 and simultaneous passage of liquid through the column.

Referring to FIG. 2B, column 30 can be rotated using a drive motor 42 to continually or discontinuously rotate vessel 30 at a desired speed. A stepper motor 44 may also be provided as shown to allow movement of vessel 30 from a horizontal to a vertical position and back again as desired.

EXAMPLE 3

DNA Synthesis

Demonstration of synthesis was obtained by performing a limited number of synthesis cycles on a 500 μmol scale. In three instances, 5'-TpsG was made (yield about 87% each time). In another instance, 5'-TpsTpsTpsG was made. For this synthesis, coupling efficiency of the second coupling was about 98%. The step-wise coupling efficiency was somewhat lower than desirable for an industrial process, but conditions were sub-optimal since the system was opened to the air for each reagent addition/removal step. Under these conditions lower than normal coupling yields are expected. Products of the above pilot experiments were characterized by routine analytical techniques and found to be representative of the expected products.

Specifically, all of the coupling chemistry was performed manually and made to be as similar to the Millipore 8800 chemistry as possible. Due to the lack of a closed system, as noted above, the conditions were sub-optimal. Using 5 grams of controlled-pore glass (CPG), a volume of 40 ml was introduced at one time.

Oligonucleotide phosphorothioates were synthesized manually using CPG as a solid support. Standard β-cyanoethylphosphoroamidite chemistry was used with a modification to include sulfurization. Reactions took place in a Kontes chromatography column (2.5 cm internal diameter by 15 cm length) with mixing by a Whatman cell culture small roller bottle apparatus. The reaction vessel was interfaced with a Millipore 8800 DNA synthesizer for solvent delivery. All solvents were maintained under as anhydrous condition as possible.

One reaction cycle, which results in the addition of a single base onto the solid support, consists of four steps. These are 1) detritylation 2) coupling 3) sulfurization and 4) capping. The CPG beads were washed after each step.

The starting material was purchased as a 5'-dimethoxytrityl deoxyguanosine controlled pore glass, pore size, 350 Å, loading 90–110 μmol/g. Volumes given are for a 500 μm synthesis. Five grams of the starting material were used. All rotations described occurred at 10 rpm.

Detritylation

The trityl protection groups were removed using deblock solution (2.5% v/v dichloroacetic acid in dichloromethane). Fifty milliliters of deblock solution were added to the CPG beads. Mixing occurred by rotation of the roller bottle apparatus for four minutes. Then the solvent was removed by flushing the reaction vessel with argon gas. This cycle was repeated approximately six times or until the CPG beads no longer were of a reddish-orange color.

After this, the beads were washed with low-water acetonitrile and mixed on the roller bottle apparatus for four minutes. Acetonitrile was removed from the reaction vessel by flushing with argon.

Coupling

Nucleoside phosphoroamidite solutions were prepared by dissolving 1g of nucleoside phosphoroamidite in 12 mls of acetonitrile. Prior to the actual coupling reaction, the CPG beads were washed once with tetrazole solution (31.8g 1-H-tetrazole/1±10%). The CPG beads were mixed on the roller bottle apparatus for four minutes then dried completely by flushing with Argon. To prepare the solution for the coupling reaction, 20 ml of the phosphoroamidite solution were added to 11.2 ml of tetrazole solution. This solution was added to the reaction vessel and mixed on the roller bottle apparatus for 25 minutes. After the reaction is complete, the CPG beads were flushed with Argon. Sixty ml of acetonitrile were used for a wash and mixed on the roller bottle apparatus for four minutes. The CPG beads were again flushed with Argon to dry.

Sulfurization

Sulfurizing reagent (aka Beaucage reagent) was prepared by dissolving commercially available 3H-1,2-benzodithiol- 3-one-1, 1-dioxide in acetonitrile to make a 0.05M solution. This reagent was stored in silanized bottles. Forty ml of the Beaucage reagent were added to the reaction vessel and mixed on the roller bottle apparatus for 5 minutes. The CPG beads were flushed with Argon. The beads were washed by mixing on the roller bottle apparatus with forty ml of acetonitrile for four minutes and dried by flushing with Argon.

Capping

The capping reaction involves two reagents, Cap A and Cap B. Cap A consists of 10% acetic anhydride and 90% tetrahydrofuran. Cap B consists of 10% pyridine, 10% N-methylimidizole and 60% tetrahydrofuran. Twenty ml of Cap A were added first to the reaction vessel. Then twenty ml of Cap B were added. The CPG beads were then mixed on the roller bottle apparatus for six minutes. The beads were dried by flushing with Argon. The beads were then washed with 60 ml of tetrahydrofuran with rotation on the roller bottle apparatus for 4 minutes. The beads were then dried by flushing with Argon.

At this point, the oligonucleotide is ready for another reaction cycle or it can be cleaved from the solid support and purified.

This working prototype demonstrates that a horizontal column can be used in a scalable process for large scale oligonucleotide synthesis. This apparatus can be readily adapted for automated fluid delivery rather than the manual delivery used. Because the columns are only limited by their internal diameter and length, the process is scalable to extremely large size as described herein.

Other Embodiments

Other embodiments are within the following claims. For example, the vessel described above is readily adapted for use in synthesis of all types of polymers, including those for making combinatorial libraries of nucleic acids, peptides, or carbohydrates, or any combination thereof. Since the chemistry of the reaction need not be changed in such a vessel, but the scale of synthesis can be increased, such vessels have significant advantages in increasing the amount of product made. The quality and yield may also be increased.

I claim:

1. A solid phase synthesizer, comprising:
   a generally horizontal and generally cylindrical elongated vessel for holding a solid support and liquid having two ends, each end having a porous blocker to prevent the solid support from leaving said vessel but allowing passage of the liquid from said vessel,
   a particulate solid support held within said vessel, having a size sufficient to prevent passage of said support through said blocker, and
   a liquid reagent with components sufficient for synthesis of a polymer selected from the group consisting of DNA, RNA, proteins, oligonucleotides, carbohydrates, and peptides, on said particulate solid support.

2. The solid phase synthesizer of claim 1 wherein said vessel has a generally smooth inner surface.

3. The solid phase synthesizer of claim 1 wherein said vessel has a generally non-smooth inner surface.

4. The solid phase synthesizer of claim 1 wherein said vessel has a serrated inner surface.

5. The solid phase synthesizer of claim 1 wherein said vessel comprises a screw held within said vessel adapted to enhance mixing of said solid support and the liquid.

6. The solid phase synthesizer of claim 1 wherein said vessel comprises blades held within said vessel, and adapted to mix said solid support and the liquid.

7. The solid phase synthesizer of claim 1 wherein said vessel comprises a mixer.

8. The solid phase synthesizer of claim 7 wherein said mixer comprises mixing bars.

9. The solid phase synthesizer of claim 1 comprising an agitator adapted to agitate said solid support and the liquid within said vessel.

10. The solid phase synthesizer of claim 1 wherein said synthesizer comprises a vibrator adapted to vibrate said solid support within said vessel and thereby enhance mixing of said solid support and the liquid.

11. The solid phase synthesizer of claim 1 wherein said synthesizer comprises a vortexer adapted to vortex said solid support and the liquid within said vessel.

12. The solid phase synthesizer of claim 1 wherein said synthesizer comprises a rocker adapted to rock said solid support and the liquid within said vessel.

13. The solid phase synthesizer of claim 12 wherein said rotator is adapted to allow different rotational speeds of said vessel.

14. The solid phase synthesizer of claim 1 comprising a rotator adapted to rotate said vessel about its horizontal axis.

15. The solid phase synthesizer of claim 1 wherein said vessel rotates at a speed sufficient to cause mixing of said solid support with the liquid but insufficient to cause significant fragmentation of said solid support.

16. The solid phase synthesizer of claim 1 comprising a positioner adapted to move said vessel from a horizontal position to a vertical position.

17. The solid phase synthesizer of claim 1 wherein said positioner is adapted to move said vessel from a vertical position to said horizontal position.

18. The solid phase synthesizer of claim 17 wherein said length is from 15 to 30 centimeters.

19. The solid phase synthesizer of claim 1 wherein said vessel has an internal length from 5 to 100 centimeters inclusive.

20. The solid phase synthesizer of claim 1 wherein said vessel has an internal diameter of from 3 to 15 centimeters inclusive.

21. The solid phase synthesizer of claim 20 wherein said diameter is 5 to 10 centimeters.

22. The solid phase synthesizer of claim 1 having a size sufficient to allow synthesis of said polymer on a scale of 20 millimoles or greater.

23. The solid phase synthesizer of claim 22 wherein said scale is 50 millimoles or greater.

24. The solid phase synthesizer of claim 23 wherein said scale is 100 millimoles or greater.

25. The solid phase synthesizer of claim 23 wherein said scale is 500 millimoles or greater.

26. The solid phase synthesizer of claim 1 wherein said synthesizer is adapted to vary the tilt of said vessel.

27. The solid phase synthesizer of claim 26 wherein said synthesizer is adapted to rock said vessel.

28. The solid phase synthesizer of claim 1 comprising a pump for provision of chemical reagents to said vessel.

29. The solid phase synthesizer of claim 28 wherein said pump provides said chemical reagents under pressure.

30. The solid phase synthesizer of claim 1 wherein said vessel is maintained under anhydrous conditions.

31. An improved method for synthesis of a polymer comprising the steps of:
   providing a solid phase synthesizer for synthesis of said polymer and introducing chemicals into said synthesizer in a desired order, the improvement comprising:

conducting said synthesis in a solid phase synthesizer comprising a generally horizontal and generally cylindrical elongated vessel for holding a solid support and liquid having two ends, each end having a porous blocker to prevent the solid support from leaving said vessel but allowing passage of the liquid from said vessel, and a particulate solid support held within said vessel, having a size sufficient to prevent passage of said support through said blocker.

32. A solid phase synthesizer, comprising:

a generally horizontal and generally cylindrical elongated vessel for holding a solid support and liquid having two ends, each end having a porous blocker to prevent the solid support from leaving said vessel but allowing passage of the liquid from said vessel;

a particulate solid support held within said vessel, having a size sufficient to prevent passage of said support through said blocker, wherein said particulate solid support is suitable for synthesis of oligodeoxyribonucleotide; and a liquid reagent with components sufficient for synthesis of an oligodeoxyribonucleotides on said particulate solid support.

33. A solid phase synthesizer, comprising:

a generally horizontal and generally cylindrical elongated vessel for holding a solid support and liquid having two ends, each end having a porous blocker to prevent the solid support from leaving said vessel but allowing passage of the liquid from said vessel;

a particulate solid support held within said vessel, having a size sufficient to prevent passage of said support through said blocker, wherein said particulate solid support is suitable for synthesis of oligoribonucleotide; and a liquid reagent with components sufficient for synthesis of an oligoribonucleotides on said particulate solid support.

34. A solid phase synthesizer, comprising:

a generally horizontal and generally cylindrical elongated vessel for holding a solid support and liquid having two ends, each end having a porous blocker to prevent the solid support from leaving said vessel but allowing passage of the liquid from said vessel;

a particulate solid support held within said vessel, having a size sufficient to prevent passage of said support through said blocker, wherein said particulate solid support is suitable for synthesis of peptide and a liquid reagent with components sufficient for synthesis of a peptide on said particulate solid support.

35. A solid phase synthesizer, comprising:

a generally horizontal elongated vessel defining a void for holding a particulate solid support and liquid, said vessel having two ends, each end having a porous blocker to prevent the solid support from leaving said void but allowing passage of the liquid from said vessel;

a particulate solid support held within said void, having a size sufficient to prevent passage of said support through said blocker; and a liquid reagent with components sufficient for synthesis of a polymer selected from the group consisting of DNA, RNA, proteins, oligonucleotides, carbohydrates, and peptides, on said particulate solid support.

36. A method for solid phase synthesis of a polymer, comprising the steps of:

providing a solid phase synthesizer comprising:

a generally horizontal elongated vessel for holding a solid support and liquid having two ends, each end having a porous blocker to prevent the solid support from leaving said vessel but allowing passage of the liquid from said vessel, and a particulate solid support held within said vessel, having a size sufficient to prevent passage of said support through said blocker, and introducing chemicals necessary for synthesis of said polymer into said vessel in an order appropriate for synthesis of said polymer.

37. The method of claim 36, wherein said vessel is rotated about its horizontal axis.

38. A method of solid phase synthesis of a polymer, comprising the steps of:

providing a solid phase synthesizer comprising:

a generally horizontal and generally cylindrical elongated vessel for holding a solid support and liquid having two ends, each end having a porous blocker to prevent the solid support from leaving said vessel but allowing passage of the liquid from said vessel, and a particulate solid support held within said vessel, having a size sufficient to prevent passage of said support through said blocker, and introducing chemicals necessary for synthesis of said polymer into said vessel in an order appropriate for synthesis of said polymer.

39. The method of claim 38, wherein said vessel is rotated about its horizontal axis.

40. A method for synthesis of a polymer, comprising the steps of:

providing reagents for the synthesis of said polymer to a solid phase synthesizer in a desired order, wherein said solid phase synthesizer comprises:

a generally horizontal elongated vessel defining a void for holding a particulate solid support and a liquid, said vessel having a first end for application of said reagents to the particles within said void, and a second end for removal of applied reagents therefrom, at least said second end having a porous blocker to prevent the solid support from leaving said vessel while allowing the passage of said reagents from said vessel, and a particulate solid support held within said void, having a size sufficient to prevent passage of said support through said blocker, and contacting the reagents with said support in an order appropriate for synthesis of said polymer under conditions sufficient to cause incremental formation of said polymer.

* * * * *

UNITED STATES PATENT AND TRADEMARK OFFICE
CERTIFICATE OF CORRECTION

PATENT NO : 5,744,102
DATED : April 28, 1998
INVENTOR(S): EADIE, James S.

It is certified that error appears in the above-identified patent and that said Letters Patent is nereby corrected as shown below:

Column 1, line 39: delete "$10_6$-$10_7$" and insert therefor --$10^6$-$10^7$--;

Column 3, line 59: delete "desireds" and insert therefor --desired--;

Claim 18, column 8, lines 34 and 35, is mis-numbered: re-number as --19.--; at line 34, delete "claim 17" and insert therefor --claim 18--; and Claim 19, column 8, lines 36 through 38, is mis-numbered: re-number as --18.--.

Signed and Sealed this

Thirteenth Day of October 1998

Attest:

BRUCE LEHMAN

Attesting Officer

Commissioner of Patents and Trademarks